US008920715B2

(12) United States Patent
Roberts et al.

(10) Patent No.: US 8,920,715 B2
(45) Date of Patent: Dec. 30, 2014

(54) STERILANT COMPOSITION AND SYSTEM

(75) Inventors: Keith Allen Roberts, White Bear Lake, MN (US); Carl William Hahn, Sugar Land, TX (US); Gabriel P. Kern, Birchwood, MN (US); Ryan A. Hoitink, St. Paul, MN (US); Robert Orvin Crowder, Lino Lakes, MN (US); John Henry Burban, Lake Elmo, MN (US)

(73) Assignee: Hemostasis, LLC, St. Paul, MN (US)

( * ) Notice: Subject to any disclaimer, the term of this patent is extended or adjusted under 35 U.S.C. 154(b) by 1979 days.

(21) Appl. No.: 11/500,202

(22) Filed: Aug. 7, 2006

(65) Prior Publication Data
US 2007/0031464 A1 Feb. 8, 2007

Related U.S. Application Data

(60) Provisional application No. 60/705,924, filed on Aug. 5, 2005.

(51) Int. Cl.
| | |
|---|---|
| *A61K 45/06* | (2006.01) |
| *A61K 33/40* | (2006.01) |
| *A01N 37/16* | (2006.01) |
| *A01N 37/26* | (2006.01) |
| *A61L 2/18* | (2006.01) |
| *A61L 2/24* | (2006.01) |
| *A61L 2/26* | (2006.01) |

(52) U.S. Cl.
CPC ............... *A61K 45/06* (2013.01); *A01N 37/16* (2013.01); *A01N 37/26* (2013.01); *A61K 33/40* (2013.01); *A61L 2/18* (2013.01); *A61L 2/186* (2013.01); *A61L 2/24* (2013.01); *A61L 2/26* (2013.01); *A61L 2202/14* (2013.01); *A61L 2202/24* (2013.01)

USPC ................... 422/16; 422/18; 422/25; 422/29; 422/292; 422/294; 424/405; 424/613; 424/660; 424/686; 424/715; 514/567; 510/109; 510/110; 510/161; 510/367; 510/375; 510/378; 510/383; 510/401; 510/402; 510/406; 568/303; 568/305; 568/308

(58) Field of Classification Search
USPC .......... 514/557; 422/16, 18, 25, 29, 292, 294; 510/109, 110, 161, 367, 375, 378, 383, 510/401, 402, 406; 548/335.1; 549/204; 564/463, 502; 568/303, 305, 558
See application file for complete search history.

(56) References Cited

U.S. PATENT DOCUMENTS

| 4,772,413 A | * | 9/1988 | Massaux et al. ............. 8/137 |
| 5,037,623 A | | 8/1991 | Schneider et al. |

(Continued)

FOREIGN PATENT DOCUMENTS

| WO | WO9418297 | * | 8/1994 | ............. C11D 3/39 |
| WO | WO 9418297 A1 | * | 8/1994 | |

OTHER PUBLICATIONS

Cocamide DEA. Product Sheet [online]. Useful Chemical, Inc. [retrieved on Nov. 20, 2009]. Retrieved from the Internet: <URL: http://www.useful-chemicals.com/?p=39>.*

*Primary Examiner* — Jane C Osweсki
(74) *Attorney, Agent, or Firm* — Denise M. Everett

(57) ABSTRACT

An antimicrobial solution for disinfecting instruments in an automatic sterilization device, the solution comprising: a peracid reaction product formed in situ from combining a liquid acetyl donor with a solid source of peroxide, wherein the in situ reaction takes place in the sterilization device, along with a containment and delivery ampule for use in an automatic sterilization device, and methods for disinfecting a medical instrument employing the inventive antibacterial solution.

14 Claims, 1 Drawing Sheet

(56) References Cited

U.S. PATENT DOCUMENTS

| | | |
|---|---|---|
| 5,077,008 A | 12/1991 | Kralovic et al. |
| 5,116,575 A * | 5/1992 | Badertscher et al. ............ 422/28 |
| 5,192,459 A * | 3/1993 | Tell et al. ....................... 424/665 |
| 5,350,563 A * | 9/1994 | Kralovic et al. ................. 422/28 |
| 5,505,740 A * | 4/1996 | Kong et al. ........................ 8/111 |
| 6,407,052 B2 * | 6/2002 | Gassenmeier et al. ......... 510/441 |
| 6,872,696 B2 * | 3/2005 | Becker et al. .................. 510/392 |
| 2001/0000251 A1 * | 4/2001 | Wei et al. ....................... 510/367 |
| 2004/0152610 A1 * | 8/2004 | Engel et al. .................... 510/296 |

\* cited by examiner

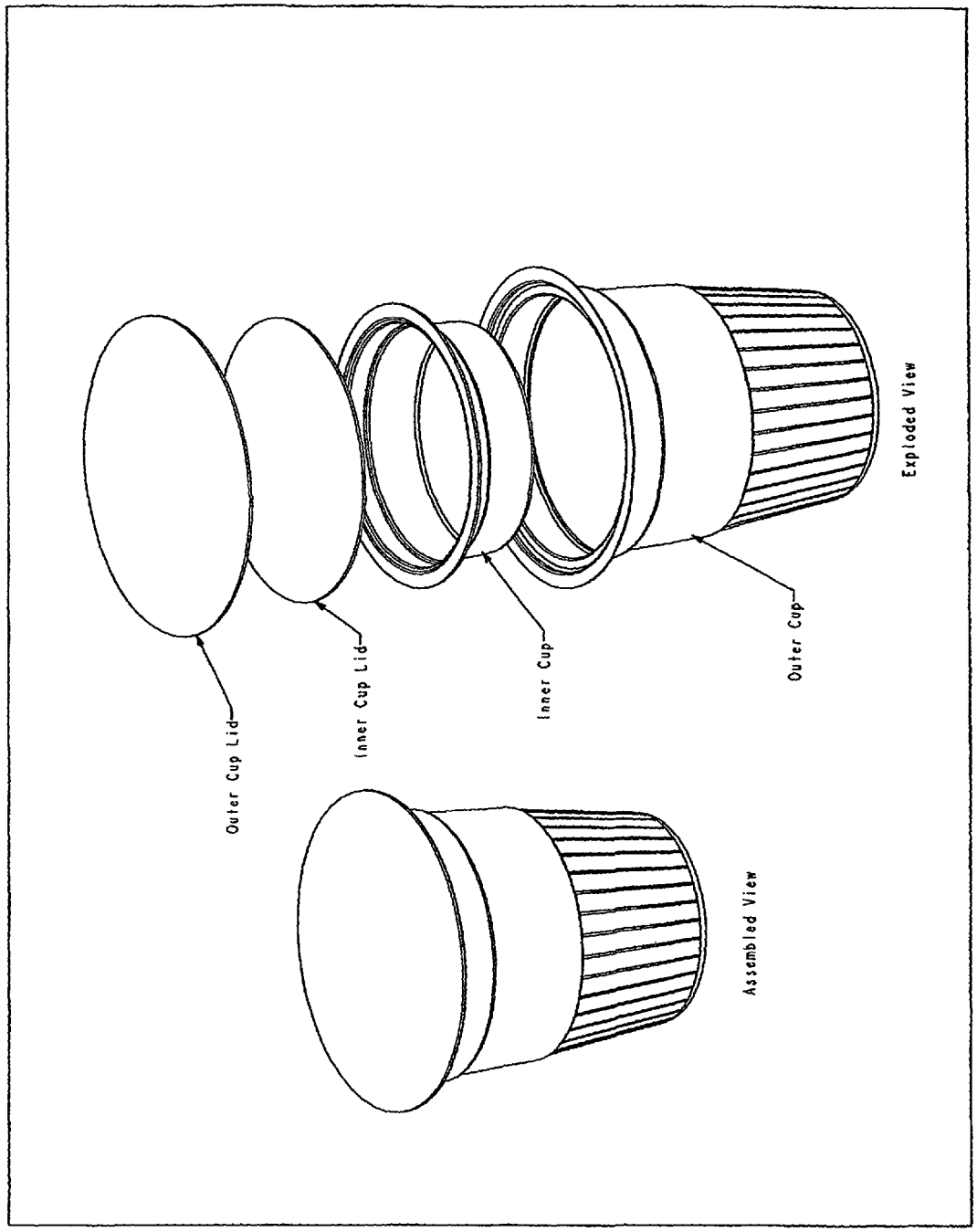

STERILANT COMPOSITION AND SYSTEM

FIELD OF THE INVENTION

The invention relates to antimicrobial compositions and sterilization systems and methods having particular application in conjunction with automated sterilization or disinfecting medical instruments.

BACKGROUND OF THE INVENTION

Devices designed for the at least partially automated sterilization of medical instruments are known in the art.

For example, the Steris One system, available from Steris Corporation of Mentor, Ohio, functions by first positioning the contaminated instrument in a chamber within the machine and attaching tubing to the fluid channels of the instrument chamber. A dose of the antimicrobial composition is inserted into the machine. An aspirator is then inserted into the top of the package that contains the antimicrobial and the lid of the machine is closed. A technician starts a cycle and a cycle consists of four stages: (1) the system plumbing is rinsed; (2) the entire interior of the machine fills with water and a circulation pump mixes the antimicrobial chemicals into the water, producing, in situ, the antimicrobial solution, and the machine heats the antimicrobial solution to a desired temperature; (3) once the antimicrobial solution reaches the desired temperature, it is circulated through the system at that temperature for a specified length of time; (4) the antimicrobial is rinsed out of the system with sterile water and the cycle is complete. The technician opens the lid and removes the sterilized, but wet instruments for immediate use.

Antimicrobial or antimicrobial solutions adapted for use in such sterilizing devices are also known, but each suffers drawbacks either in terms of storage, handling, and corrosiveness, or compromised capability of rapid in situ dissolution of the composition components. Typically, known antimicrobial systems rely on peracetic acid or other strong oxidants as the sterilizing agent.

Peracetic acid is an unstable compound prone to decomposition into acetic acid and hydrogen peroxide, which upon further decomposition produces oxygen gas. The decomposition products have minimal biocidal activity as compared to peracetic acid. In order to minimize the decomposition rate and improve its shelf life, manufacturers of peracetic acid typically add about 1% sulfuric acid to the peracetic acid. This increases corrosiveness of the antimicrobial and necessitates the addition of extra buffers and corrosion inhibitors. In addition, containers for peracetic acid must be vented to permit escape of the oxygen gas and prevent a problematic rise in pressure. In addition to the vents allowing the escape of the oxygen gas, the vents also allow for the escape of the concentrated peracetic acid vapors, which are noxious, explosive, and potentially harmful. Storage conditions which may subject the peracetic acid container to increases in temperature must be avoided, and storage of containers which vent materials into the atmosphere is problematic and subject to additional regulatory intervention.

U.S. Pat. No. 5,077,008 to Kralovic et al. discloses an antimicrobial solution comprising, inter alia, a strong oxidant selected from organic peroxides, peracids, chloride releasing compounds, chlorine dioxide, hyperchlorides and phenol, and a particular anti-corrosive system. Peracetic acid or combinations of peracetic acid with other oxidants are disclosed as preferred oxidant components. This patent teaches a specific, synergistic corrosion inhibiting system that comprises at least two specific corrosion inhibitors, one of which is preferably a phosphate, but between phosphates, molybdates and triazoles. Other components include buffering agents, sequestering agents, and wetting agents. However, this antimicrobial delivery system is subject to the known disadvantages of using reactive liquid reagents.

U.S. Pat. No. 5,037,623 to Schneider et al. discloses ampule-based systems for maintaining reactive components and reagents separately until immediately prior to use. Schneider teaches use of a vented, liquid-containing ampule which may be disposed in any orientation without leaking liquid. The preferred antimicrobial is peracetic acid. The vent insures that the pressure within the ampule does not become so great that it ruptures during storage and/or handling. The vent is situated on the ampule such that liquid does not leak from the vent aperture regardless of the orientation of the ampule. However, storage of ampules which continually vent poses additional challenges, and the oxidant in this system is still subject to continual degradation which may be enhanced by environment conditions.

Other systems have been designed to circumvent the disadvantages to vented liquid ampules which rely on powdered ingredients to the antimicrobial composition. For example, U.S. Pat. No. 5,116,575 to Badertscher teaches a dry composition of powdered ingredients, including a powdered borate and a powdered water soluble acid precursor, along with the use of dry reagents, including an acetylsalicylic acid precursor and a sodium perborate peroxide source, and steps requiring the utilization of powdered acetylsalicylic acid and a powdered perborate. Badertscher also discloses a sterilization apparatus including a receiving station for receiving the dry ingredients and a disposable ampule-based delivery, but requires that the ingredients which form the oxidant component be sealed in the ampule in powdered form. Here, the strong oxidant is delivered via a powdered precursor. However, there are drawbacks to the utilization of powdered ingredients intended for in situ dissolution. The amount of time required for effective dissolution of solid ingredients into a water solvent is greater and less consistent than that for liquid ingredients.

The dry reagent receiving region is connected to a water supply which selectively flows through and dissolves the dry reagents in the reagent receiving region forming the microorganism killing oxidant solution. All the ingredients which dissolve to form the oxidant solution are present in the reagent receiving region. The ampules supply a premeasured dose of powdered reagents. In system designs wherein flowing water is relied on to dissolve dry ingredients, concentrations of components in the resulting antimicrobial solution will vary over time according to solubility.

Hence, there is a need in the art for antimicrobial systems which overcome these and other disadvantages.

SUMMARY OF THE INVENTION

Accordingly, the present inventive antimicrobial system delivers a water-soluble peracetic acid precursor, for example, diacetyl methylamine (DAMA), in liquid form, to the antimicrobial solution. Sodium percarbonate, or some other peroxide source, is delivered in a dry/solid form. When combined to form the antimicrobial composition, these ingredients react in situ to form peracetic acid (PAA), the antimicrobial agent. Other peracid antimicrobials can be generated in situ by any suitable choice of the liquid peracid precursor and the powdered hydrogen peroxide source.

The inventive antimicrobial composition comprises precursor reagents which form the sterilizing oxidant, for example, liquid DAMA and a peroxide source, such as percarbonate or perborate. These precursor ingredients are held in separate compartments within a containment cup/ampule. The antimicrobial system is adapted via this specialized cup to deliver the DAMA in liquid form (see FIG. 1). The inventive antimicrobial methods utilize a specialized containment and delivery ampule for the composition ingredients which are adapted to operate with commercially available automated instrument sterilizing machines and, in particular, the Steris System One Machine and its known and unknown equivalents.

DAMA, an inherently stable liquid peracid precursor component, does not have the decomposition and handling disadvantages typical of other known liquid-peracid systems. Further, the shelf life with respect to the biocidal activity of the sterilizing oxidant is increased with avoidance of decomposition issues. In addition, the present antimicrobial composition does not require the addition of sulfuric acid or the equivalent, and therefore requires the addition of fewer corrosion inhibitors than known compositions.

Certain aspects of the present antimicrobial system and composition are depicted in the following drawing. The drawing, however, is an illustration of particular embodiments and should not be construed as limiting the scope of the invention as disclosed herein and as defined by the claim.

BRIEF DESCRIPTION OF THE DRAWING

FIG. 1: Illustrates one embodiment of a cup or ampule design comprising a two-chambered thermoformed cup, which permits delivery of the liquid peracid precursor agent and other solid reagents in an antimicrobial system.

DETAILED DESCRIPTION OF THE PREFERRED EMBODIMENT

The invention provides an antimicrobial solution for use in conjunction with automated sterilization devices, known and unknown. Certain embodiments of the inventive antimicrobial solution and methods are intended to be compatible with the currently marketed Steris System One machine, manufactured by Steris Corporation of Mentor, Ohio. However, the invention may be readily adapted for use in similarly functioning devices. These devices perform to achieve various levels of commercial disinfection and sterilization of instruments, for example, medical instruments.

Medical device disinfecting and sterilization, particularly with respect to re-useable medical devices, is a highly regulated activity. The seminal industry guide as to the relevant definitions, requirements, and regulations is "Content and Format of Premarket Notification Submissions for Liquid Chemical Sterilants/High Level Disinfectants," which is published by the U.S. Food and Drug Administration, and may be found at http://www.fda.gov/cdrh/ode/397.html, the content of which is fully incorporated herein by reference.

One embodiment of the invention is directed to an antimicrobial solution for disinfecting instruments in an automatic sterilization device. The solution comprises: a peracid reaction product formed in situ from combining a liquid acetyl donor with a powdered or granulated solid source of peroxide. For purposes of defining the invention, the term "granulated" is meant to include a variety of solid forms including, for example, beads, pellets, and tablets. By "in situ" it is meant that the reaction yielding the strong oxidant takes place in the sterilization device. The inventive antimicrobial solution may further comprise one or more of the following: an acidic pH modifier; a corrosion inhibitor; optionally, at least one wetting agent; at least one chelating agent; and at least one anti-redeposition agent comprising a polymer. Examples of such polymers suitable for use in the present invention include, but are not limited to, hydroxycarboxylic polymer and sodium poly-alpha-hydroxyacrylate. Other suitable polymers are well-known in the art. Preferred amounts include from about 0.5% to about 2% by weight of the solution.

Peracetic acid (PAA) is a strong sterilizing oxidant approved for use in sterilizing medical instruments. The peracid liquid acetyl donor according to the present invention may comprise, for example, any acetyl donor that may exist in stable form as a liquid. In specific embodiments, the peracid liquid acetyl donor may be diacetyl methylamine, capraloctone, and imidazole. According to a very specific embodiment, the liquid acetyl donor comprises diacetyl methylamine (DAMA).

DAMA is an organic liquid peroxy compound precursor which is water soluble and readily reacts with conventional inorganic persalt compounds, such as percarbonate, to generate PAA. It is known in the art that liquid dispersions of DAMA have the advantage over dry granular compositions of PAA precursors in that they react more readily when added to water to produce PAA, and also exhibit improved dispersability in water. According to specific embodiments, the peroxide source may comprise a percarbonate or a perborate, and the cation may be any suitable cations, including, for example, sodium. In a very specific embodiment, the peroxide source is sodium perborate. The selection of a peroxide source may affect the desirability and/or suitability of other ingredients. For example, if the peroxide source is a percarbonate, the corrosion inhibitor may comprise a phosphate, but if the peroxide source is a perborate, the corrosion inhibitor is typically not a phosphate.

The reaction between a peracetic acid precursor, such as DAMA, and a peroxide source such as a perborate, proceeds at a faster rate at caustic pH values, generally above a pH of about 8. However, the amount of gas generated by the decomposition of the various ingredients is greater at these same pH values, and may result in unacceptable levels of gas formation at pH's above about 8. The amount of gas generated may affect the operation of the sterilizing machine and thus the amount may need to be limited. Hence, it is desirable to limit the pH of the reaction conditions to about 8, and the pH modifier may be introduced into the solution in a way that maintains the optimal in situ reaction condition pH of about 8. In one embodiment of the invention, it is desirable for the reaction of the peracetic acid precursor, DAMA, with the peroxide source, to occur before the dissolution of the pH modifying acid. A specific non-limiting example of a suitable acidic pH modifying agent is citric acid.

Accordingly, one embodiment of the present inventive method provides that the reactive components react at an elevated pH to rapidly produce the peracetic acid and then the reaction condition pH is decreased rapidly when the pH modifying agent, for example, citric acid, is introduced, reducing the subsequent generation of gaseous components. In a specific embodiment, a controlled release mechanism is employed for the introduction of some or all of the pH modifying acid ingredient. Non-limiting examples of suitable controlled release mechanisms suitable for employment in the present invention include encapsulating the acidic pH modifier in a water-soluble capsule that dissolves in a time and/or pH-dependent manner, packaging the acidic pH modifier in a water-soluble pouch, tableting the acidic pH modifier, or by physically separating the acidic pH modifying ingredient from the reaction location and using machine logic to control the amount and rate of addition as the reaction progresses. For example, the logic may include sensitivity to pH. According to one specific embodiment, the controlled release mechanism comprises use of gelatin-based capsules. Film, made from polyvinyl alcohol, can be used to make a water-soluble pouch that is suitable for this invention. Selection of the chemical and physical properties of a controlled release agent in order to affect the degree to which the dissolution of the acid will be suppressed will be obvious to those of ordinary skill in the art.

In one embodiment of the present invention, the goal is to produce oxidant in concentrations sufficient to achieve commercial sterility of the instrument at standard operating conditions of the automated sterilization device. Commercial sterility may be achieved as a result of varying several factors of the sterilization method, including concentration of oxidant in the antimicrobial solution, volume and pressure of the solution flow according to the sterilant device parameters, and time the instrument remains immersed or otherwise in contact with the antimicrobial solution. An important consideration is post-immersion conditions, including, for example, rinse conditions and the sterile rating of the rinse solution and the provision of drying means. Under standard operating conditions of known automated sterilization devices, commercial sterility may be achieved by concentrations of PAA of about 2,000 ppm and greater.

In one specific embodiment, the antimicrobial solution further comprises citric acid as a pH modifier, and may comprise cocamide DEA, a widely used commercially available surfactant to improve the wetting ability of the solution and to provide some corrosion protection for steel. In other specific embodiments, the antimicrobial composition comprises at least one ingredient to prevent precipitates in cases where hard water is used and at least one ingredient to provide corrosion protection for steel and copper. In a very specific embodiment the precipitate preventative and/or a corrosion protectant comprises sodium polyphosphate. Specific embodiments additionally comprise benzotriazole, which is a known corrosion inhibitor for copper, brass and aluminum.

The invention also provides a specialized containment and delivery cup, or ampule (see FIG. 1), adapted for use in the automated disinfecting/sterilizing device. One embodiment is directed to a two-compartment containment and delivery ampule employable in an automated sterilization device. The ampule comprises a first compartment having an interior, and a second compartment having an interior, wherein the interiors of the first and second compartments are not in communication with one another, and further wherein the first compartment contains a liquid peracid precursor reagent, and the second compartment comprises a powdered or granulated solid peroxide source reagent. The reagents are located in the interiors of the respective compartments. The compartment containing the liquid peracid precursor reagent is sealed.

According to another embodiment, the inventive ampule further comprises an outer cup enclosing an outer cup volume and an inner cup enclosing an inner cup volume. The first compartment is defined by the inner cup enclosing the inner cup volume, the inner cup being entirely disposed within the outer cup, and the outer compartment is defined by the outer cup enclosing a volume equal to the outer cup volume minus the inner cup volume.

In a specific embodiment the sealed inner cup contains the liquid peracid precursor reagent, and in a very specific embodiment the reagent is DAMA. According to a further specific embodiment, the remaining ingredients are packaged together in the outer cup (see FIG. 1 "outer cup"). In one very specific embodiment, all ingredients contained within the outer cup are powders. If a wetting agent is included as an ingredient and the wetting agent is a liquid and is stable in the presence of the peracid precursor liquid, then it may be packaged within the liquid-containing inner cup. Otherwise it may be packaged with the powders. In a further very specific embodiment, the solution comprises cocamide DEA and all ingredients contained within the outer cup are powders except the cocamide DEA, which is contained as a viscous liquid in the outer cup. In one embodiment a quantity of PAA, the antimicrobial agent, sufficient to achieve the desired sterilization concentration (above 2000 ppm), is produced in situ when the DAMA and sodium percarbonate mix and react in the water introduced into the sterilizing device, for example, into a Steris System One Machine or its known and unknown equivalents. The outer cup containing the source of solid peroxide source may contain a vent that would allow for the release of any oxygen gas produced by decomposition of the peroxide source. The vent mechanism for the outer cup may include but is not limited to a simple aperture, a one way check-valve, or a permeable outer lid to the outer cup.

Once employed properly in the Steris System One Machine or its equivalent, a quantity of peracetic acid, the antimicrobial agent, sufficient to provide suitable sterilizing capacity (above 2000 ppm), is produced in situ when the DAMA and peroxide source, for example, sodium percarbonate, dissolve and react in the approximately 11.8 liters of water that is introduced according to specifications of the Steris System One operation. How to make appropriate adjustments to the composition to maintain sufficient concentrations of the antimicrobial agent will be readily apparent to one of ordinary skill in the art in the case of system changes which introduce different amounts of water.

The invention also provides a method of disinfecting an instrument, such as a medical device, using an antimicrobial solution formulated for use in an automated sterilization device. According to one embodiment, the method comprises: mixing a liquid peracid precursor agent and a solid peroxide source whereby the liquid peracid precursor reagent and the solid peroxide source react to form peracetic acid, and wherein a substantially constant concentration of peracetic acid in the antimicrobial solution sufficient to reach commercial sterility of the instrument is achieved and maintained by, for example, addition of an acidic pH modifier subject. The instrument is immersed in the antimicrobial solution until commercial sterility is reached. The acidic pH modifier may be added to the reagent solution in a pH, or time-dependent matter, subject, for example, to a controlled release mechanism, that is capable, therefore, of maintaining the reaction at a pH of approximately 8, such that undesirable gas formation is minimized. According to another method embodiment, the liquid peracid precursor reagent is sealed in a first compartment, while solid ingredients, including the peroxide source along with any desired corrosion inhibitor, an optional at least one wetting agent, and the at least one chelating agent, are sealed in a second compartment. The contents of the first and second compartments are kept separated until an instrument is to be disinfected. In a specific embodiment, the liquid peracid precursor reagent comprises DAMA, the peroxide source comprises perborate, and the controlled-release acid pH modifier comprises citric acid.

The following examples illustrate specific embodiments of the inventive antimicrobial composition and should not be construed as limiting the scope of the invention as set forth herein and as defined by the claims.

Example 1

This example, detailed in Table 1, illustrates a specific embodiment of the present inventive antimicrobial composition.

TABLE 1

Formulation Ingredients for a Antimicrobial Composition

| Compound | Function | Weight % in Concentrate | Weight % in 11.8 liters aqueous solution |
|---|---|---|---|
| Sodium percarbonate | source of peroxide to react with DAMA | 42.6 | 0.958 |
| DAMA (diacetyl methyl amine) | reacts to form PAA (peracetic acid) | 33.2 | 0.746 |
| Citric Acid | pH adjuster | 17.0 | 0.381 |
| Tergitol MinFoam2x | wetting agent | 1.9 | 0.042 |
| Sodium polyphosphate | sequestering agent and corrosion inhibitor | 0.9 | 0.020 |
| Benzotriazole | corrosion inhibitor for copper and brass | 3.5 | 0.080 |
| EDTA | Chelating and sequestering agent | 0.9 | 0.020 |

Citric acid, or other suitable pH modifiers, is used to adjust the pH of the solution, a parameter that influences the rate of reaction, the corrosiveness of the solution and the gas generation of the resulting antimicrobial solution. Tergitol MinFoam2x is a commercially available surfactant that improves the wetting ability of the solution. Sodium polyphosphate is added to prevent precipitates in cases where hard water is used and also provides corrosion protection for steel and copper. Benzotriazole is a corrosion inhibitor for copper, brass, and aluminum. The EDTA is a chelating and sequestering agent and is added to prevent precipitates in cases where hard water is used and also chelates metals that can accelerate the decomposition of the peracetic acid.

Example 2

This example, detailed in Table 2, illustrates a second specific embodiment of the present inventive antimicrobial composition.

TABLE 2

Formulation Ingredients for a Antimicrobial Composition

| Compound | Function | Weight % in Concentrate | Weight % in 11.8 liters aqueous solution |
|---|---|---|---|
| Sodium perborate | source of peroxide to react with DAMA | 39.8 | 0.746 |
| DAMA (diacetyl methyl amine) | reacts to form PAA (peracetic acid) | 34.7 | 0.651 |
| Citric Acid | pH adjuster | 19.4 | 0.364 |
| Cocamide DEA | wetting agent and corrosion inhibitor | 0.1 | 0.001 |
| EDTA | Chelating and sequestering agent | 1.4 | 0.027 |
| Benzotriazole | corrosion inhibitor for copper and brass | 4.5 | 0.084 |

Citric acid, or other suitable pH modifiers, is used to adjust the pH of the solution, a parameter that influences the rate of reaction, the corrosiveness of the solution and the stability of the resulting antimicrobial solution. Cocamide DEA is a commercially available surfactant that improves the wetting ability of the solution and provides some corrosion protection for steel. The EDTA is added to prevent precipitates in cases where hard water is used and also chelates metals that can accelerate the decomposition of the peracetic acid. Benzotriazole is a corrosion inhibitor for copper, brass, and aluminum.

The invention claimed is:

1. An antimicrobial solution effective for sterilization of instruments in an automatic sterilization device, the solution comprising:
   a peracid product formed in situ from combining a liquid acetyl donor selected from the group consisting of diacetyl methylamine, caprolactone, and imidazole with a powdered or granulated solid source of peroxide, and
   an acidic pH modifier that is introduced into the solution via a controlled release mechanism to maintain an optimal in situ reaction condition pH of about 8,
   wherein the in situ reaction takes place in the sterilization device and wherein the concentration of peracid product formed in situ is effective to achieve sterilizing concentrations of at least about 2000 ppm without addition of sulfuric acid.

2. The antimicrobial solution according to claim 1, further comprising one or more of:
   a corrosion inhibitor;
   at least one wetting agent; and
   at least one chelating agent.

3. The antimicrobial solution according to claim 1, further comprising at least one anti-redeposition agent comprising a polymer.

4. The antimicrobial solution according to claim 1, wherein the liquid acetyl donor comprises diacetyl methylamine.

5. The antimicrobial solution according to claim 1, wherein the source of peroxide is selected from the group consisting of a percarbonate and a perborate.

6. The antimicrobial solution according to claim 5, wherein the source of peroxide is a perborate.

7. The antimicrobial solution according to claim 5, wherein if the peroxide source is a percarbonate, the corrosion inhibitor may comprise a phosphate, but if the peroxide source is a perborate, the corrosion inhibitor is not a phosphate.

8. The antimicrobial solution according to claim 1 wherein the acidic pH modifier comprises citric acid.

9. The antimicrobial solution according to claim 1, wherein the controlled release mechanism comprises one of: encapsulating the acidic pH modifier in a water-soluble capsule; packaging the acidic pH modifier in a water-soluble pouch; forming the acidic pH modifier into a tablet; or employing machine logic to deliver the acidic pH modifier to the solution in a time- or pH-dependent manner.

10. The antimicrobial solution according to claim 9, wherein the controlled release mechanism comprises packaging the acidic pH modifier in a water soluble pouch.

11. The antimicrobial solution according to claim 10, wherein the water soluble pouch comprises a polyvinyl alcohol.

12. The antimicrobial solution according to claim 2 comprising a wetting agent, wherein the wetting agent comprises cocamide DEA.

13. The antimicrobial solution according to claim 1, wherein the reaction product comprises peracetic acid and the reaction takes place at reaction conditions which result in a generation of peracetic acid at a level sufficient to achieve commercial sterility of the instrument at standard operating conditions of the automated sterilization device.

14. The antimicrobial solution according to claim 1, wherein the liquid acetyl donor comprises diacetyl methylamine (DAMA), the solid granulated or powdered peroxide source comprises perborate, and the acidic pH modifier comprises citric acid, and further wherein the concentrations of DAMA, perborate and citric acid are manipulated so that the antimicrobial solution contains peracetic acid in concentrations sufficient to achieve commercial sterility of the instrument at standard operating conditions of the automatic sterilization device.

* * * * *